United States Patent [19]

Fedorov et al.

[11] Patent Number: 5,346,507
[45] Date of Patent: * Sep. 13, 1994

[54] INTRAOCULAR LENS AND A POLYMER COMPOSITION FOR MAKING SAME

[76] Inventors: Svyatoslav N. Fedorov, pereulok Dostoevskogo, I/2I,kv.32; Leonid F. Linnik, ulitsa Deguninskaya,17,kv.36, both of Moscow; Givi D. Shimshlashvili, ulitsa Machabeli,II., Tbilisi; Valentina S. Starshinova, Karelsky bulvar,24,kv.75., Moscow; Pavel P. Zak, Telegrafny pereulok,II/I6,kv.6I., Moscow; Mikhail A. Ostrovsky, ulitsa 26 Bakinskikh komissarov,II,kv.90., Moscow; Irina B. Fedorovich, ulitsa Dmitria Ulyanova,3,kv.I46., Moscow; Valentina A. Roslyakova, ulitsa Griboedova,21,kv.22.; Valentin V. Guzeev, prospekt Pobedy,I/2,kv.I5., both of Dzerzhinsk; Alexandr I. Dyachkov, ulitsa Kljukvina,5,kv.39., Gorkovskaya oblast, Dzerzhinsk; Irina I. Afanasieva, ulitsa Uritskogo,I2-a,kv.50., Gorkovskaya oblast, Dzerzhinsk; Vera S. Ljusina, ulitsa Stroitelei,3,kv.I3I., Gorkovskaya oblast, Dzerzhinsk; Evgeny I. Degtev, Yaroslavskoe shosse,14,kv.34., Moscow, all of U.S.S.R.

[*] Notice: The portion of the term of this patent subsequent to Mar. 13, 2010 has been disclaimed.

[21] Appl. No.: 671,716

[22] PCT Filed: Jul. 27, 1989

[86] PCT No.: PCT/SU89/00201

§ 371 Date: Apr. 3, 1991

§ 102(e) Date: Apr. 3, 1991

[87] PCT Pub. No.: WO91/01696

PCT Pub. Date: Feb. 21, 1991

[51] Int. Cl.$^5$ .............................................. A61F 2/16
[52] U.S. Cl. ............................................ 623/6; 623/66
[58] Field of Search ................................. 623/66, 6

[56] References Cited

U.S. PATENT DOCUMENTS

| | | | |
|---|---|---|---|
| 4,716,234 | 12/1987 | Dunks et al. | 623/6 |
| 4,753,654 | 6/1988 | Posin et al. | 623/6 |
| 4,822,359 | 4/1989 | Tano et al. | 623/6 |

FOREIGN PATENT DOCUMENTS

| | | | |
|---|---|---|---|
| 0259532 | 9/1986 | European Pat. Off. | 623/6 |
| 0280215 | 2/1987 | European Pat. Off. | 623/6 |

*Primary Examiner*—David Isabella
*Assistant Examiner*—Debra S. Brittingham

[57] ABSTRACT

An intraocular lens comprises a UV-absorbing optic lens made of a polymer composition having the following light transmission spectrum in its visible position at the following wavelengths: 400 nm, 10 to 27 percent of light transmission; 420 nm, 21 to 37 percent; 440 nm, 37 to 55 percent; 460 nm, 52 to 63 percent; 480 nm, 70 to 78 percent; 500 nm, 85 to 90 percent; 520 to 650 nm, 90 to 95 percent, and incorporating ingredients taken in the following mass percent ratio:

| | |
|---|---|
| UV-absorbing material (4-alkoxy-2-hydroxybenzophenone or tetraoxybenzophenone) | 1.65 to 3.0 |
| fat-soluble dye-4-(2,4-dimethylphenylazo)-5-methyl-2-phenyl-1,2,3-triazole | 0.011 to 0.016 |
| dibutylphthalate | 4.8 to 5.0 |
| polymethylmethacrylate | to make up 100%. |

1 Claim, No Drawings

1

INTRAOCULAR LENS AND A POLYMER COMPOSITION FOR MAKING SAME

FIELD OF THE INVENTION

The present invention relates generally to ophthalmology and more specifically to an intraocular lens for correction of sight after an operative ablation of the natural crystalline lens, as well as to a polymer composition for making said intraocular lens.

BACKGROUND OF THE INVENTION

Known in the present state of the art are intraocular lenses whose optic lenses are made of polymethylmethacrylate and provide for optical eye correction after removal of the natural crystalline lens.

However, such intraocular lenses fail to protect the retina from being damaged by UV or short-wavelength visible light.

The closest to the herein-proposed intraocular lens are UV-400 lenses, comprising a UV-absorbing optic lens made of a polymethylmethacrylate-based polymer composition and a UV-absorbing substance, such as 2,4-dihydroxybenzophenone.

Such optic lenses protect the retina against damage by light at wavelengths shorter than 380 nm, while such intraocular lenses closely resemble, in the visible light spectrum, natural crystalline lenses of young people aged under the age of 25 and feature the following transmission factor values on a wavelength of: 400 nm, 1.5 percent, 420 nm, 55 percent; 440 nm, 82 percent, while on wavelengths in the range of 460 to 650 nm said factor is within 93 and 95 percent.

However, with the aforesaid light transmission percentage values of the known intraocular lenses an excess amount of light gets into the eye within a range of 400 to 480 nm, which precludes obtaining to the greatest extent of restoration of visual acuity and color perception nor does it enable one to bring to a normal level the protection of the retina against damage with light waves shorter than 480 nm in patients over the age of 25. Besides, the polymer composition used for making such intraocular lenses fails to produce such lenses that would correspond, as for their spectral characteristics, to the natural crystalline lenses of people older than 25.

SUMMARY OF THE INVENTION

It is an object of the present invention to provide an intraocular lens and a polymer composition for making the same, which would make it possible to obtain an optic lens that would correspond, as for its spectral characteristics, to the natural crystalline lenses of people over the age of 25 and that, when implanted, would increase the degree of restoration of visual acuity and color perception.

In keeping with the foregoing and further objects, in an intraocular lens, comprising a UV-absorbing optic lens, according to the invention, said optic lens is made of a material featuring the following light transmission spectrum in its visible portion at the following wavelengths: 400 nm, 10 to 27 percent of light transmission; 420 nm, 21 to 37 percent; 440 nm, 37 to 55 percent, 460 nm, 52 to 63 percent; 480 nm, 70 to 78 percent; 500 nm, 85 to 90 percent; 520 to 650 nm, 90 to 95 percent.

Said object is accomplished also due to the fact that in a polymer composition for making said intraocular lens, incorporating polymethylmethacrylate and a UV-absorbing material, according to the invention, said polymer composition comprises, as said UV-absorbing material, 4-alkoxy-2-hydroxybenzophenone or tetraoxybenzophenone, and incorporates additionally a fat-soluble dye, such as, 4-(2,4-dimethylphenylazo)-5-methyl-2-phenyl-1,2,3-triazole, as well as dibutylphthalate as a plasticizer, with the following ratio of the aforesaid ingredients (in mass percent):

Practical application of the proposed intraocular lens having the aforesaid light transmission spectrum of its optical lens provides for transmission of blue light equivalent to its transmission by the natural crystalline lenses of people older than 25, which ensures more complete restoration of visual acuity and color perception, as well as renders the coursing of the postoperative period milder and cuts down its duration. In addition, the proposed intraocular lenses protect the retina against premature ageing and adds to visual comfort.

Use of the proposed polymer composition for making intraocular lenses, due to an appropriately selected qualitative and quantitative ratio of its ingredients, provides for obtaining the abovementioned spectral characteristics of the proposed intraocular lens, which are based on the combination of the spectral properties of the proposed dye and UV-absorbing material, the aforesaid spectral characteristics within a range of 430 to 650 nm being ensured due to the spectral properties of said dye, and those within a range of 380 to 430 nm, due to combination of the spectral properties of the dye and of the UV-absorbing material.

Any increase or decrease in the limits of the ingredients making part of the aforesaid composition results in optic lens spectral characteristics which go beyond the proposed limits, which affects adversely visual acuity and color perception in patients and leads to injuries to the retina by the light having a wavelength shorter than 380 nm.

The aforesaid percentage ratios between the ingredients incorporated into the proposed polymer composition are decisive in judging whether the formulations of the composition agree with the spectral characteristics of the proposed intraocular lens, so that the limiting values of the composition formulation depend on the thickness of the optic lens of said intraocular lens, that is, the lower limiting values of the composition ingredients refer to thick (500 to 630$\mu$m) intraocular lenses, the upper limiting values refer to 'thin' (300 to 380m) intraocular lenses, and the intermediate values refer to 'medium' (400 to 480$\mu$m) intraocular lenses, as indicated in Table 1 hereinbelow.

In the proposed composition the UV-absorbing material (i.e., 4-alkoxy-2-hydroxybenzophenone or tetraoxybenzophenone) takes part in formation of the intraocular lens spectral characteristics (that is, restricts penetration of short-wavelength light onto the retina), as well as serves a light-stabilizer of the dye against possible fading. Apart from its conventional application as a plasticizer, dibutylphthalate is used also as an additional UV-absorbing material.

The fat-soluble dye, i.e., 4-(2,4-dimethulphenylazo)-5-methyl-2-phenyl-1,2,3-triazole has the following structural formula:

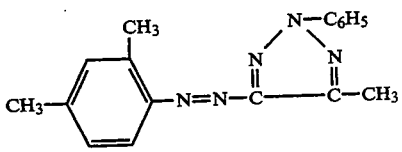

Said dye is hydrophobic, stains the polymer composition uniformly and provides for optical purity of the lens with a preset light transmission spectrum, since the dye neither reflects nor diffuses light and moreover it is not washed out of the optic lens.

Thus, intraocular lenses made from the proposed polymer material, are nontoxic and optically pure, they correspond, as for their spectral characteristics, to natural crystalline lenses of people over the age of 25, and provide for more complete rehabilitation of the visual functions of patients after implantation of such lenses.

DETAILED DESCRIPTION OF THE INVENTION

For a better understanding of the present invention, given below are the following examples of specific practical embodiment thereof given by way of illustration.

The intraocular lens comprises a UV-absorbing optic lens made of a material featuring the following light transmission spectrum in its visible portion at the following wavelengths: 400 nm, 10 to 27 percent; 420nm, 21 to 37 percent; 440nm, 37 to 55 percent; 460nm, 52 to 63 percent; 480nm, 70 to 80 percent; 500nm, 85 to 90 percent; 520 to 650nm, 90 to 95 percent, a 50-percent transmission point lying within a wavelength range of 430 and 455nm.

To produce an intraocular lens with such a light transmission spectrum of its optic lens, use is made of a polymer composition, incorporating polymethylmethacrylate, a UV-absorbing material, a fat-soluble dye, i.e., 4-(2,4-dimethylphenylazo-5-methyl-2-phenyl-1,2,3-triazole, and dibutylphthalate as a plasticizer, with the following ratio of the aforesaid ingredients (in mass percent):

| | |
|---|---|
| UV-absorbing material | 1.65 to 3.0 |
| fat-soluble dye | 0.011 to 0.016 |
| dibutylphthalate | 4.8 to 5.0 |
| polymethylmethactylate | to make up 100%, | wherein the aforesaid UV-absorbing material is 4-alkoxy-2-hydroxybenzophenone or tetraoxybenzophenone.

Exemplary compositions for making the proposed intraocular lenses are produced by the method of en-block radiation-induced polymerization in the presence of isobutyric acid azodinitrile as a polymerization initiator.

EXAMPLE 1

There are taken weighed portions of the reaction mixture initial constituents in the following amounts: methylmethacrylate, 93.274 g; fat-soluble dye, i.e. 4-(2,4-dimethylphenylazo)-5-methyl-2-phenyl-1,2,3-triazole, 0.016 g; UV-absorbing material, i.e., 4-alkoxy-2-hydroxybenzophenone, 1.65 g; dibutylphatalate-plasticizer, 5 g; polymerization initiator (isobutyric acid azodinitrile), 0.06 g. The aforelisted ingredients are placed in a glass flask at room temperature and are made to completely dissolve in methylmethacylate under constant stirring by a mechanical agitator. Then the mixture is passed through a capron filter, vacuumized at a residual pressure of 120 to 140 mm Hg and cast in moulds composed of two polished silicate glass pieces provided with a spacer in the form of a PVC tube arranged along the mould perimeter. Moulds filled with the mixture are placed in an air-fed polymerization cabinet. The polymerization process proceeds for 10 to 12 hours.

Upon completion of polymerization the moulds are discharged from the polymerization cabinet and the finished specimen is separated from the silicate glass, thus obtaining the polymer composition incorporating the following ingredients (in mass percent):

| | |
|---|---|
| polymethylmethacrylate | 93.334 |
| UV-absorbing material-4-alkoxy-2-hydroxybenzophenone | 1.65 |
| fat-soluble dye-4-(2,4-dimethylphenylazo)-5-methyl-2-phenyl-1,2,3-triazole | 0.016 |
| dibutylphthalate | 5.0. |

EXAMPLE 2

There are taken weighed portions of the reaction mixture initial constituents in the following amounts: methylmethacrylate, 92.926 g; fat-soluble dye, i.e., 4-(2,4-dimethylphenylazo)-5-methyl-2-phenyl-1,2,3-triazole, 0.014 g; UV-absorbing material, i.e., tetraoxylbenzophenone, 2.10 g; dibutylphathalate as a plasticizer, 4.9 g; polymerization initiator, i.e., isobutyric acid azodinitrile, 0.06 g. The ingredients are intermixed and polymerization is carried out according to the procedure described in Example 1. The result is the polymer composition composed of the following ingredients (in mass percent);

| | |
|---|---|
| polymethylmethacrylate | 92.986 |
| UV-absorbing material-4-alkoxy-2-hydroxybenzophenone | 2.10 |
| fat-soluble dye-4-(2,4-dimethylpheylazo)-5-methyl-2-phenyl-1,2,3-triazole | 0.014 |
| dibutylphthalate | 4.90 |

EXAMPLE 3

There are taken weighed portions of the reaction mixture initial constituents in the following amounts: methylmethacrylate, 92.528 g; fat-soluble dye, i.e., 4-(2,4-dimethylphenylazo)-5-methyl-2-phenyl-1,2,3-triazole, 0.012 g; UV-absorbing material, i.e., 4-alkoxy-2-hydroxybenzophenone, 2.60 g; dibutylphthalate as a plasticizer, 4.8 g; polymerization initiator, i.e. isobutyric acid azodinitrile, 0.06 g. The ingredients are intermixed and polymerization is carried out according to the procedure described in Example 1. The result is the polymer made up of the following ingredients (in mass percent):

| | |
|---|---|
| polymethylmethacrylate | 92.588 |
| UV-absorbing material-4-alkoxy-2-hydroxybenzophenone | 2.60 |
| fat-soluble dye-4-(2,4-dimethylphenylazo)-5-methyl-2-phenyl-1,2,3-triazole | 0.012 |
| dibutylphthalate | 4.80 |

EXAMPLE 4

There are taken weighed portions of the reaction mixture initial components in the following amounts: methylmethacrylate, 92.129 g; fat-soluble dye, i.e., 4-(2,4-dimethylphenylazo)-5-methyl-2-phenyl-1,2,3-triazole, 0.011 g; UV-absorbing material, i.e., tetraoxybenzophenone, 3.00 g; dibutylphthalate, 4.8 g; polymerization initiator, i.e. isobutyric acid azodinitrile, 0.06 g. The ingredients are intermixed and polymerization is carried out according to the procedure described in Example 1. The result is the polymer composition made up of the following ingredients (in mass percent):

| | |
|---|---|
| polymethacrylate | 92.189 |
| UV-absorbing material-tetraoxybenzophenone | 3.00 |
| fat-soluble dye-4-(2,4-dimethylphenylazo)-5-methyl-2-phenyl-1,2,3-triazole | 0.011 |
| dibutylphthalate | 4.80 |

Intraocular lenses made of the polymer composition prepared as described in Examples 1 to 4, feature the aforementioned light transmission spectra whose parameters are ensured due to an appropriate ration of the ingredients making part of said composition, as well as depend on the thickness of a given intraocular lens (i.e., on its dioptic power and on the thickness of a specific model of the intraocular lens). For instance, Table 1 contains data on light transmission by the optic lens of the intraocular lens versus said dye content of the polymer composition.

TABLE 1

| | Light transmission percent at a given ratio between dioptric power (D), thickness of intraocular lens across the central axis, μm and dye concentration, % | | | |
|---|---|---|---|---|
| Light wavelength, nm | 7–10 D, 300 to 380 μm 0.016% | 11–12 D, 400 to 420 μm, 0.014% | 13–15 D, 440 to 480 μm, 0.012% | 16–25 D, 500 to 630 μm, 0.011% |
| under 360 | not over 0.014% | | | |
| 380 | not over 0.5 | | | |
| 400 | 25 to 27 | 24 to 26 | 24 to 27 | 10 to 23 |
| 420 | 28 to 37 | 29 to 31 | 28 to 32 | 21 to 32 |
| 440 | 38 to 55 | 38 to 40 | 38 to 42 | 37 to 50 |
| 460 | 54 to 63 | 54 to 56 | 54 to 58 | 52 to 57 |
| 480 | 73 to 78 | 74 to 75 | 75 to 76 | 70 to 76 |
| 500 | 87 to 90 | 87 to 88 | 87 to 88 | 85 to 88 |
| 520 | 92 to 94 | 92 to 93 | 92 to 93 | 90 to 93 |
| 540 to 650 | 94 to 95 | 94 to 95 | 94 to 95 | 94 to 95 |

With the limiting values of the amount of the dye specified for a given dioptric power, the spectral characteristic of the optic lens will go beyond the limits proposed herein, which will affect adversely the patient's visual acuity and color perception.

According to the trials performed, practical application of the material for the optic lens of the intraocular lens featuring the abovementioned spectral characteristics adds to the degree of visual acuity restoration by 10 to 25 percent compared with the prototype. Table 2 presents the findings of experiments carried out on 12 advanced-age patients with pseudoaphakia. The patients' visual acuity was estimated by the ratio between the distances at which a tabular Landolt's ring can be distinguished when looked at through a light filter featuring the herein-proposed spectral characteristics and through another light filter having the spectral characteristic of the prototype, the estimation being carried out according to one of the commonly adopted techniques. All measurements were performed in daylight.

TABLE 2

| | | Visual acuity with spectral characteristics: | | |
|---|---|---|---|---|
| | | proposed intraocular lens according to limiting values: | | |
| Nos | Patient's age | short wavelength | long wavelength | prototype |
| 1 | 49 | 1.14 | 1.18 | 1.02 |
| 2 | 63 | 1.10 | 1.27 | 1.06 |
| 3 | 50 | 1.20 | 1.31 | 1.04 |
| 4 | 57 | 1.20 | 1.37 | 1.05 |
| 5 | 70 | 1.21 | 1.40 | 1.05 |
| 6 | 62 | 1.21 | 1.45 | 1.07 |
| 7 | 50 | 1.11 | 1.24 | 1.02 |
| 8 | 51 | 1.18 | 1.35 | 1.04 |
| 9 | 60 | 1.19 | 1.39 | 1.04 |
| 10 | 80 | 1.10 | 1.25 | 1.03 |
| 11 | 65 | 1.10 | 1.21 | 1.04 |
| 12 | 59 | 1.04 | 1.11 | 1.02 |

According to the evidence contained in Table 2, a percentage increase in visual acuity is 25.4±2.7 on the average, compared with the prototype for the long-wavelength limiting value of the spectral characteristics of the proposed intraocular lens, and 11±1.5 for the short-wavelength limiting value.

The adopted ratios between the ingredients of light-filtering additives making part of the polymer composition, and the dioptric power of the proposed optic lens of the intraocular lens enable one to produce intraocular lens with due account of prognosticated age-dependent changes in the spectral characteristics of natural crystalline lenses.

Thus, the chief features of the invention are the light transmission factors within the wavelength range of 420 to 520 nm, ensured due to the qualitative and quantitative characteristics of the proposed polymer composition. Table 3 contains comparative data on light transmission factors of the proposed intraocular lens and of the prototype intraocular lens.

TABLE 3

| Light wavelength, nm | Light transmission, % | |
|---|---|---|
| | Proposed intraocular lens | Prototype |
| 420 | 21 to 37 | 55 |
| 440 | 37 to 55 | 82 |
| 460 | 52 to 63 | 93 |
| 480 | 70 to 78 | 95 |
| 500 | 85 to 90 | 95 |
| 520 | 90 to 94 | 95 |

An analysis into the light transmission spectra of natural crystalline lenses, of the proposed intraocular lenses, and of the prototype has demonstrated that the proposed intraocular lenses correspond, as for their spectral characteristics, to the natural crystalline lenses in people aged 50 and over. It is due to the abovesaid fact that the optic lens of the proposed intraocular lens provides for a normal degree of optical protection afforded to the retina against damage by light in the wavelength range of 420 to 480 nm in advanced-age people whose retina is to a greater extent vulnerable by luminous radiation. Thereby the amount of light absorbed by the retinal blue-sensitive cones within a range of 420 to 480 nm is reduced by 40 percent compared with the prototype. This gives evidence that the proposed intraocular lens provides for more complete restoration of patient's color perception and fuller protection of the retina against detrimental effect of light. The proposed intraocular lenses are readily implanted in patients of any age, making allowance for future age dependent changes of the patient's natural crystalline lenses.

INDUSTRIAL APPLICABILITY

The polymer composition can be used for making intraocular lense of any models based on polymethylmethacrylate which provide for optical eye correction after removal of the natural crystalline lens.

We claim:

1. An intraocular lens comprising a UV-absorbing optic lens comprising polymethylmethacrylate, 4-alkoxy-2-hydroxybenzophenone or tetraoxybenzophenone as a UV-absorbing material, 4-(2,4-dimethylphenylazo)-5-methyl-2-phenyl-1,2,3-triazole, and dibutylphthalate as a plasticizer, said components being present in the following weight percent ratio:

| | |
|---|---|
| UV-absorbing material | 1.65 to 3.0 |
| 4-(2,4-dimethylphenylazo)-5-methyl-2-phenyl-1,2,3-triazole | 0.011 to 0.016 |
| dibutylphthalate | 4.8 to 5.0 |
| polymethylmethacrylate | balance | wherein the lens is made of a material having the following light transmission spectrum in its visible portion at the following wave lengths:

400 nm—10 to 27 percent of light transmission;
420 nm—21 to 37 percent;
440 nm—37 to 55 percent;
460 nm—52 to 63 percent;
480 nm—70 to 78 percent;
500 nm—85 to 90 percent; and
520–650 nm—90 to 95 percent.

* * * * *